(12) United States Patent
Mikos et al.

(10) Patent No.: US 7,629,388 B2
(45) Date of Patent: *Dec. 8, 2009

(54) SYNTHESIS AND CHARACTERIZATION OF BIODEGRADABLE CATIONIC POLY(PROPYLENE FUMARATE-CO-ETHYLENE GLYCOL) COPOLYMER HYDROGELS MODIFIED WITH AGMATINE FOR ENHANCED CELL ADHESION

(75) Inventors: Antonios G. Mikos, Houston, TX (US); Kazuhiro Tanahashi, Houston, TX (US)

(73) Assignee: William Marsh Rice University, Houston, TX (US)

(*) Notice: Subject to any disclaimer, the term of this patent is extended or adjusted under 35 U.S.C. 154(b) by 448 days.

This patent is subject to a terminal disclaimer.

(21) Appl. No.: 10/300,202

(22) Filed: Nov. 20, 2002

(65) Prior Publication Data

US 2003/0152548 A1 Aug. 14, 2003

Related U.S. Application Data

(60) Provisional application No. 60/375,270, filed on Apr. 24, 2002, provisional application No. 60/331,668, filed on Nov. 20, 2001.

(51) Int. Cl.
*A67K 47/00* (2006.01)
*A01N 25/00* (2006.01)

(52) U.S. Cl. .............. 514/772.3; 514/772; 514/772.1; 514/772.6; 514/779

(58) Field of Classification Search .................. None
See application file for complete search history.

(56) References Cited

U.S. PATENT DOCUMENTS 3,701,748 A 10/1972 Kroekel (Continued)

FOREIGN PATENT DOCUMENTS

DE 2061421 12/1970

(Continued)

OTHER PUBLICATIONS

Kikuchi et al., *Adhesion and Proliferation of Bovine Aortic Endothelial Cells on Monoamine- and Diamine-containing Polystyrene Derivatives*, J. Biomater Sci. Polymer Edn, vol. 3, pp. 253-260 (1992).

(Continued)

*Primary Examiner*—Eric E. Silverman
(74) *Attorney, Agent, or Firm*—Conley Rose, P.C.; Rodney B. Carroll

(57) ABSTRACT

A cross-linkable monomer comprises a fumaric acid functional group having a first end and a second end, a first spacer group affixed to said first end and comprising at least repeating unit, a first terminal group affixed to said first spacer group, a second spacer group affixed to said second end and comprising at least one ethylene glycol repeating unit, and a second terminal group affixed to said second spacer group. A hydrogel formed by cross-linking the present monomer and a method for making the monomer. A method for forming a hydrogel, comprises the steps of a) synthesizing a copolymer of poly(propylene fumarate) (PPF) and poly(ethylene glycol) (PEG) so as to produce P(PF-co-EG), b) synthesizing a PEG-tethered fumarate (PEGF), c) coupling agmatine sulfate to the PEGF to produce PEGF modified with agmatine (Agm-PEGF), and d) cross-linking the P(PF-co-EG) from step a) with Agm-PEGF from step c).

17 Claims, 7 Drawing Sheets

U.S. PATENT DOCUMENTS

| | | | |
|---|---|---|---|
| 4,720,338 | A | 1/1988 | Newman et al. |
| 4,722,948 | A | 2/1988 | Sanderson |
| 4,843,112 | A | 6/1989 | Gerhart et al. |
| 4,888,413 | A | 12/1989 | Domb |
| 5,162,430 | A | 11/1992 | Rhee et al. |
| 5,278,063 | A | 1/1994 | Hubbell et al. |
| 5,286,763 | A | 2/1994 | Gerhart et al. |
| 5,364,627 | A | 11/1994 | Song |
| 5,420,179 | A | 5/1995 | Fourquier et al. |
| 5,512,600 | A | 4/1996 | Mikos et al. |
| 5,514,378 | A | 5/1996 | Mikos et al. |
| 5,522,895 | A | 6/1996 | Mikos |
| 5,527,864 | A | 6/1996 | Suggs et al. |
| 5,573,934 | A | 11/1996 | Hubbell et al. |
| 5,644,005 | A | 7/1997 | Suggs et al. |
| 5,696,175 | A | 12/1997 | Mikos et al. |
| 5,733,951 | A | 3/1998 | Yaszeniski et al. |
| 5,874,500 | A | 2/1999 | Rhee et al. |
| 5,945,457 | A | 8/1999 | Plate et al. |
| 5,986,043 | A | 11/1999 | Hubbell et al. |
| 5,989,579 | A | 11/1999 | Darougar et al. |
| 5,998,362 | A | 12/1999 | Feng et al. |
| 6,028,164 | A | 2/2000 | Loomis |
| 6,071,982 | A | 6/2000 | Wise et al. |
| 6,072,022 | A | 6/2000 | O'Brien et al. |
| 6,123,373 | A | 9/2000 | Yoshida |
| 6,124,373 | A | 9/2000 | Peter et al. |
| 6,153,664 | A | 11/2000 | Wise et al. |
| 6,166,184 | A * | 12/2000 | Hendriks et al. ............ 530/356 |
| 6,283,997 | B1 | 9/2001 | Garg et al. |
| 6,306,821 | B1 * | 10/2001 | Mikos et al. .................... 514/2 |
| 6,355,755 | B1 | 3/2002 | Peter et al. |
| 6,384,105 | B1 | 5/2002 | He et al. |
| 6,423,790 | B1 | 7/2002 | He et al. |
| 6,685,957 | B1 * | 2/2004 | Bezemer et al. ............. 424/426 |
| 6,753,358 | B2 | 6/2004 | Fisher et al. |
| 6,759,485 | B2 | 7/2004 | He et al. |
| 6,884,778 | B2 | 4/2005 | Jo et al. |

FOREIGN PATENT DOCUMENTS

| | | | |
|---|---|---|---|
| EP | 0325866 | A1 | 8/1989 |
| EP | 0580328 | A2 | 1/1994 |
| WO | WO 95/29710 | | 11/1995 |
| WO | WO 00/62630 | * | 10/2000 |

OTHER PUBLICATIONS

Vuento et al., *Isolation of a Novel Cell-Attachment and Spreading-Promoting Protein From Human Serum*, Bioche. J. (1985) vol. 227, pp. 421-427.

Whateley et al., *Isolation of a Serum Componenet that Stimulates the Spreading of Cells in Culture*, Biochem. J. (1980) vol. 185, pp. 349-354.

Augusta et al., *Synthesis and Antibacterial Activity of Immobilized Quaternary Ammonium Salts*, Journal of Applied Polymer Science, vol. 53 pp. 1149-1163 (1994).

Felding-Haberman et al., *Vitronectin and Its Receptors*, Current Opinion in Cell Biology 1993, 5:864-868.

Boughton et al., *The Biochemical and Functional Heterogeneity of Circulating Human Plasma Fibronectin*, Biochemical and Biophysical Research Communications vol. 119, No. 3, (1984) pp. 1174-1180.

Lemieux et al., *Block and Graft Copolymers and Nanogel™ Copoymer Networks for DNA Delivery into Cell*, Journal of Drug Targeting 2000, vol. 8, No. 2, pp. 91-105.

Baker et al., *Equilibrium Swelling Properties of Weakly Ionizable 2-Hydroxyethyl Methacrylate (HEMA)—Based Hydrogels*, Journal of Applied Polymer Science, vol. 52, pp. 783-788 (1994).

Kokoro Lio et al., *Swelling Characteristics of a Blend Hydrogel Made of Poly(allylbiguanido-co-allylamine) and Poly(vinyl alcohol)*, Polymer vol. 36 No. 13 (1995) pp. 2579-2583.

Uchida et al., *Sorption of Low-Molecular-Weight Anions into Thin Polycation Layers Grafted onto a Film*, Langmuir (1993), 9, pp. 1121-1124.

Graham et al., *Interaction of Poly(ethylene oxide) with solvents: 2. Water-poly(ethylene glycol)*, Polymer (1989) vol. 30, pp. 528-533.

Miyamoto et al., *Fibronectin and Integrins in Cell Adhesion, Signaling, and Morphogenesis*, Annals New York Academy of Sciences (6 p.).

Grinnell, *Focal Adhesion Sites and the Removal of Substratum-bound Fibronectin*, Journal of Cell Biology, vol. 103 (No. 6, Pt. 2) Dec. 1986, pp. 2697-2706.

Graham et al., *Interaction of poly(ethylene oxide) with Solvents: 4. Interaction of Water with Poly (ethylene oxide) Crosslinked Hydrogels*, Polymer, 1990, vol. 31 pp. 909-916.

Grinnell et al., *Fibroblast Receptor for Cell-Substratum Adhesion: Studies on the Interaction of Baby Hamster Kidney Cells with Latex Beads Coated by Cold Insoluble Globulin (Plasma Fibronectin)*, Journal of Cell Biology, vol. 86 Jul. 1980, pp. 104-112.

Raasch et al., *Biological Significance of Agmatine, an Endogenous Ligand at Imidazoline Binding Sites*, British Journal of Pharmacology (2001) 133, pp. 755-780.

Blantz et al., *Biological Effects of Arginine Metabolites*, Acta Physiol. Scand. 2000, 168, pp. 21-25.

Khare et al., *Investigation of Hydrogel Water in Polyelectrolyte Gels Using Differential Scanning Calorimetry*, Polymer 1993, vol. 34 No. 22, pp. 4736-4739.

Atassi et al., *Synthesis of Tolerogenic Monomethoxypolyethylene Glycol and Polyvinyl Alcohol Conjugaets of Peptides*, Journal of Protein Chemistry, vol. 10, No. 6 (1991) pp. 623-627.

Ruiz et al., *Synthesis and Properties of Hydrogels from Poly (Vinyl Alcohol) and Ethylenediaminetetraacetic Dianhydride*, Polymer 42 (2001) pp. 6347-6354.

Kulik et al., *In Vitro Platelet Adhesion to Nonionic and Ionic Hydrogels With Different Water Contents*, Journal of Biomedical Materials Research, vol. 30, pp. 295-304 (1996).

He et al., *Synthesis of biodegradable poly(propylene fumarate) networks with poly(propylene fumarate)- diacrylate macromers as crosslinking agents and characterization of their degradation products*, Polymer 42 (2001) 1251-1260.

Kharas et al., *Synthesis and Characterization of Fumarte-Based Polyesters for Use in Bioresonbable Bone Cement Composites*: Journal of Applied Polymer Science, vol. 66, 1123-1137 (1997).

A C Ibay, C E. Whalley, R A Miller, H Carr, Jr , and G C Battistone "Synthesis and Properties of Polymers for Biodegradable Implants", XP-001070092:. U S. Army Institute of Dental Research Walter Reed Army Medical Center, Washington, D.C. 20307-5300; pp. 505-509; 1985.

Abraham J. Domb. Nitza Manor and Omar Elmalak ; "Biodegradable Bone Cement Compositions Based on Acrylate and Epoxide Terminated Poly(propylenen Fumarate) Oligomers and Calcium Salt Compositions", The Hebrew University of Jerusalem, School of Pharmacy—Faculty of Medicine, Department of Pharmaceutical Chemistry, Jerusalem 91120, Israel; Biomaterials 1996, vol. 17 No. 4; pp. 411417; Received Jan. 3, 1994 / Accepted Apr. 24, 1995.

Blackburn, Carol C., et al., "Carbohydrate-specific Cell Adhesion Is Mediated by Immobilized Glycolipids," The Journal of Biological Chemistry, vol. 258, No. 2 (Jan. 25, 1983), pp. 1180-1188.

Miyamoto et al., *Fibronectin and Integrins in Cell Adhesion, Signaling, and Morphogenesis*, Annals New York Academy of Sciences (6 p.), 1998.

Baker et al., *Synthetic Hydrogels: 2. Copolymers of Carboxyl-, Lactam- and Amide-Containing Monomers—Structure/Property Relationships*, Polymer 1988, 2914 (pp. 691-700).

Bajpai, *Swelling-Deswelling Behavior of Poly(Acrylamide-co-Maleic Acid) Hydrogels*, Journal of Applied Polmer Science, vol. 80, pp. 2782-2789 (2001).

Gemeinhart et al., *pH-Sensitivity of Fast Responsive Superporous Hydrogels*, Journal of Biomater. Sc. Polymer Edn. vol. 11, No. 12, pp. 1371-1380 (2000).

Zalipsky et al., *Attachment of Drugs to Polyethylene Glycols*, Eur. Polym. J. vol. 19, No. 12, pp. 117-1183 (1983).

Mori et al., *The Influence of Heparinized Polymers on the Retention of Platelets Aggregability During Storage*, Journal of Biomedical Materials Research, vol. 16, pp. 209-218 (1982).

Shin et al., *Modulation of Marrow Stromal Osteoblast Adhesion on Biomimetic Oligo[Poly(Ethylene Glycol) Fumarate] Hydrogels Modified with Arg-Gly-Asp Peptides and a Poly(Ethylene Glycol) Spacer*, Student Research Award in the Doctoral Degree Candidate Category, 28th Annual Meeting of the Society for Biomaterials, Tampa, FL, Apr. 24-27, 2002.

S. Jo et al., *Synthesis of Poly(ethylene Glycol)-Tethered Poly(Propylene Fumarate) and its Modification with GRGD Peptide*, Polymer 41 (2001) pp. 7595-7604.

Suggs et al., *Platelet Adhesion on a Bioresorable Poly(Propylene Fumarate-Co-Ethylene Glycol) Copolymer*, Biomaterials 20 (1999) pp. 683-690.

Godbey et al., *Poly(ethylenimine) and its Role in Gene Delivery*, Journal of Controlled Release 60 (1999) pp. 149-160.

Shung et al, *Kinetics of Poly(Propylene Fumarate) Synthesis by Step Polymerization of Diethyl Fumarate and Propylene Glycol Using Zinc Chloride as a Catalyst*, Journal of Biomater. Sci. Polmer Edn, vol. 13, No. 1, pp. 95-108 (2002).

Suggs et al., *Preparation and Characterization of Poly(Propylene Fumarate-Co-Ethylene Glycol) Hydrogels*, Journal of Biomater. Sci. Polymer Edn, vol. 9, No. 7, pp. 653-666 (1998).

Suggs et al., *Development of Poly(Propylene Fumarate-co-Ethylene Glycol) as an Injectable Carrier for Endothelial Cells*, Cell Transplantaion, vol. 8, pp. 345-350 (1999).

Suggs et al., *Synthesis and Characterization of a Block copolymer Consisting of Poly(Propylene fumarate) and Poly(Ethylene Glycol)*, Macromolecules vol. 30, No. 15 pp. 4318-4323 (1997).

Suggs et al., *In Vitro Cytotoxicity and in Vivo Biocompatibility of Poly(Propylene fumarate-Co-Ethylene Glycol) Hydrogels*, 1999 John Wiley & Sons, Inc. pp. 22-27, 32.

Suggs et al., *In Vitro and in Vivo Degradationof Poly(Propylene Fumarate-Co-Ethylene Glycol) Hydrogels*, 1998 John Wiley &Sons, Inc. pp. 312-320.

Tanahashi et al., *Cell Adhesion on Poly(Propylene Fumarate-Co-Ethylene Glycol) Hydrogels*, 2002 Wiley Periodicals, Inc. pp. 558-566.

* cited by examiner

SYNTHESIS AND CHARACTERIZATION OF BIODEGRADABLE CATIONIC POLY(PROPYLENE FUMARATE-CO-ETHYLENE GLYCOL) COPOLYMER HYDROGELS MODIFIED WITH AGMATINE FOR ENHANCED CELL ADHESION

CROSS-REFERENCE TO RELATED APPLICATIONS

This application claims benefit of U.S. provisional applications No. 60/331,668, filed on Nov. 20, 2001, and entitled "Crosslinkable Compounds With Guanidino Groups" and No. 60/375,270, filed on Apr. 24, 2002, and entitled "Synthesis and Characterization of Biodegradable Cationic Poly(propylene fumarate-co-ethylene glycol) Copolymer Hydrogels Modified with Agmatine for Enhanced Cell Adhesion," each of which is incorporated herein in its entirety.

STATEMENT REGARDING FEDERALLY SPONSORED RESEARCH OR DEVELOPMENT

Research leading to the present invention was supported in part by the federal government under Grant No. R01-DE13031 awarded by the National Institutes of Health. The United States government may have certain rights in the invention.

TECHNICAL FIELD OF THE INVENTION

This invention relates generally to the formation of a hydrogel having desirable swelling and cell adhesion properties, and more specifically to the provision of a degradable, in situ cross-linkable cell carrier.

BACKGROUND OF THE INVENTION

Current medical technology includes a variety of devices that can be implanted in the body. One family of implantable devices are constructed of polymeric materials having desirable physical properties, including the ability to polymerize in situ, the ability to absorb water, biodegradability etc. Depending on the application, it may further be desirable to provide an implantable device with surface properties that enhance cell adhesion. To date, however, an implantable material having properties that are optimal for certain applications has not been known.

Polymeric materials carrying cationic groups have been investigated for possible applications as cell carriers, blood compatible coating, anti-microbial materials, and as drug delivery systems. It has been reported that cationic modifications of polymeric materials tend to enhance cell adhesion because phospholipids and proteoglycans that are present on cell surfaces are negatively charged.

Mori et al. have demonstrated that surface modification of medical devices with cationic polymers could immobilize negatively charged heparin, thus reducing the surface thrombogenecity due to a gradual release of heparin.(2) Augusta et al. have reported that sucrose methacrylate hydrogels modified with quaternary ammonium salts exhibited a bactericidal effect on gram positive and gram negative bacteria. (3) Applications of polycations such as poly(spermine), poly(L-lysine), and poly(2-dimethylaminoethyl methacrylate) for local gene delivery have been summarized in recent reviews. (4,5)

In addition, various hydrogels have been investigated for their applications as cell carriers to regenerate tissues. Biodegradability and biocompatiblility important parameters in the design of hydrogel materials for tissue engineering applications. However, the cationic hydrogels of previous investigations have been non-degradable.

Poly(propylene fumarate-co-ethylene glycol) (P(PF-co-EG)) has been proposed as an injectable biodegradable polyester. The fumarate double bond enables the copolymer cross-linking. The minimal temperature increase exhibited by P(PF-co-EG) during cross-linking in the presence of water makes P(PF-co-EG) suitable for use as a cell carrier. It has been shown that a hydrogel consisting of P(PF-co-EG) and N-vinylpyrrolidone exhibits bulk degradation. When the P(PF-co-EG) hydrogel was subcutaneously implanted in rats, it elicited a minimal inflammation response. (11-13)

However, when the hydrophilicity of a P(PF-co-EG) hydrogel was increased by increasing the molar ratio of the ethylene glycol repeating unit to the propylene fumarate repeating unit of the P(PF-co-EG) copolymers, cell adhesion to the surface of the hydrogels decreased. (15) Furthermore, hydrogel modifiers such as cationic monomers have been limited by their possible toxicity. Therefore, there remains a need for a hydrogel having the desired physical traits, including hydrophilicity and enhanced cell adhesion.

SUMMARY OF THE INVENTION

The present invention provides a polymerizable monomer and a hydrogel made from that monomer. The hydrogel composition has the desired traits of in situ polymerizability, biodegradability, and hydrophilicity, as well as enhanced cell adhesion. The present hydrogels are suitable as in situ cross-linkable cell carriers for various applications in which cell-adhesion is desirable, such as embolization.

According to one preferred embodiment, cell adhesion to P(PF-co-EG) hydrogels is improved by modifying the P(PF-co-EG) hydrogels with agmatine. Since cells may grow on the surface as well as the inside of the hydrogel, the present invention includes a technique for bulk modification of P(PF-co-EG) hydrogels. It has been discovered that a hydrogel supporting cell adhesion can be prepared by cross-linking P(PF-co-EG) copolymer and a degradable macromer modified with agmatine. By way of example, an agmatine-modified poly(ethylene glycol)-tethered macromer was synthesized for the preparation of P(PF-co-EG) hydrogels with positive charges. Positive charges from the incorporated agmatine had a generally positive effect on P(PF-co-EG) hydrogel swelling.

Positively charged biodegradable hydrogels were synthesized by cross-linking of agmatine-modified poly(ethylene glycol)-tethered fumarate (Agm-PEGF) and poly(propylene fumarate-co-ethylene glycol) (P(PF-co-EG)) in order to allow investigation of the effect of the guanidino groups of the agmatine on hydrogel swelling behavior and smooth muscle cell adhesion to the hydrogels. It was found that the weight swelling ratio of the present hydrogels increased moderately and the cell adhesion increased significantly as the initial Agm-PEGF of the composition increased.

BRIEF DESCRIPTION OF THE DRAWINGS

For a more detailed description of the preferred embodiments, reference is made to the accompanying Figures, wherein:

FIG. 6A is a linear plot for the overall timecourse and FIG. 6B is a double logarithmic plot for the early phase.

DETAILED DESCRIPTION OF THE PREFERRED EMBODIMENTS

The present invention includes a composition and a method for forming a hydrogel having desirable properties of in situ polymerizability, biodegradability, and hydrophilicity, and cell adhesion.

According to one embodiment of the present invention, a cross-linkable monomer is provided which includes a fumaric acid functional group having a first end and a second end, first and second spacer groups affixed to the first and second ends, respectively, a first terminal group affixed to the first spacer group, and a second terminal group affixed to said second spacer group.

The first and second spacer groups each preferably comprise at least one ethylene glycol unit and preferably several ethylene glycol units. The spacer length is determined by the number of repeating units present in the spacer group and is preferably selected in such as way as to i) facilitate the interaction of the terminal group with cell receptors for enhancing adhesion and modulating cell function and/or ii) facilitate water swelling, and/or iii) facilitate the release of bioactive molecules that are entrapped in the hydrogel. While ethylene glycol is a preferred repeating unit, other suitable moieties can be used, including but not limited to propylene glycol or any other diol. The first and second spacer groups can be the same or different lengths and each preferably comprises at least three ethylene glycol units.

Similarly, the first and second terminal groups can be the same or different, and are each selected from the group consisting of protein fragments, whole proteins, carbohydrates, plasmid DNA, amino acids, amino acid derivatives, and peptide sequences. A terminal group that has been found to be particularly suitable for enhancing cell adhesion is agmatine. In one embodiment, one terminal group is selected to be agmatine and the other terminal group is selected to have a positive charge so as to enhance water swelling. In another embodiment, at least one of said first and second terminal groups comprises a bioactive molecule.

Figure 1:
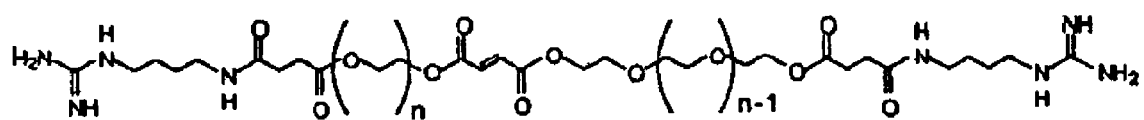
FIG. 1 is a chemical diagram of one embodiment of a monomer in accordance with the present invention.

In one preferred embodiment of the invention, a novel in situ cross-linkable, degradable macromer is modified with agmatine (Agm-PEGF) and the resulting composition used to fabricate degradable positively-charged hydrogels. For example, when P(PF-co-EG) is used as the macromer, hydrogels having desirable cell adhesion properties can be fabricated from Agm-PEGF and P(PF-co-EG) copolymer. A molecule embodying a preferred composition for the present monomer is shown schematically in FIG. 1.

The present invention further comprises a method for making the preferred monomer and for forming hydrogels by cross-linking the monomer. One embodiment of the present method comprises a) synthesizing a copolymer of poly(propylene fumarate) (PPF) and poly(ethylene glycol) (PEG) so as to produce P(PF-co-EG), b) synthesizing a PEG-tethered fumarate (PEGF), c) coupling agmatine sulfate to the PEGF to produce PEGF modified with agmatine (Agm-PEGF); and d) cross-linking the P(PF-co-EG) from step a) with Agm-PEGF from step c). The cross-linking can be carried be carried out in vivo if desired.

Hydrogels made according to the present invention preferably comprise fumarate-based polyesters modified with agmatine. In certain embodiments, the fumarate-based polyester is P(PF-co-EG) and the Agm-PEGF content of the composition is preferably an amount sufficient to allow at least 70% cell adhesion when an initial seeding density of $7.0 \times 10^3$ cells/cm$^2$ is used. In other embodiments, the fumarate-based polyester is P(PF-co-EG) and the Agm-PEGF content of the composition is preferably at least 0.1 mg/g of P(PF-co-EG) and more preferably at least 0.7 mg/g of P(PF-co-EG). The present monomers and hydrogels can be used as carriers for cells, drugs, or genes.

A cationic macromer based on fumarate and PEG is preferred because P(PF-co-EG) hydrogels have been reported to be biocompatible in vivo. Other suitable macromers include poly(propylene fumarate-co-ethylene glycol), poly(propylene fumarate-co-propylene glycol), oligo(propylene fumarate-co-ethylene glycol), oligo(propylene fumarate-co-propylene glycol), oligo(poly(ethylene glycol) fumarate), oligo(poly(propylene glycol) fumarate). The macromer is degradable at the ester bond and cross-linkable at the carbon-carbon double bond. Furthermore, the two hydroxyl groups at both terminals are useful for further modifications with biological molecules such as peptides. Likewise, other modifiers that can be incorporated into the hydrogel for the purpose of increasing cell adhesion include agmatine-modified poly(ethylene glycol) acrylate, agmatine-modified poly(ethylene glycol) methacrylate and the like.

The effect of the guanidino groups of agmatine on the swelling behavior of the cross-linked hydrogels and cell adhesion to the hydrogels was confirmed by measuring the swelling ratio of the hydrogels swollen at various pH and the water uptake in the course of swelling and quantifying the number of adhered smooth muscle cells on the hydrogels. We further compared the results of modified hydrogels with various initial Agm-PEGF contents with those of the unmodified hydrogel.

The water solubility and chain mobility of the macromer may be altered by varying the PEG chain length. GPC analysis of the resulting product obtained by the transesterification of diethylfumarate with PEG300 indicates that the product is PEG300-tethered fumarate (PEGF). The GPC chromatogram shows that the major component of the resulting product is PEG-tethered fumarate (FIG. 3A). Although the molecular weights of the succinylated PEGF and NHS are 1500 and 115, respectively, the number average molecular weight of the succinimidyl ester, 1900, was higher than expected. This result is consistent with a previous study which reported that the molecular weight of the succinimidyl ester of PEG-tethered PPF ($M_n$ of 5,900) was 7,600, 1.3-fold higher than that of the PEG-tethered PPF.

According to one preferred embodiment, one technique for fabricating a hydrogel having the desired properties comprises synthesizing a copolymer of poly(propylene fumarate) (PPF) and poly(ethylene glycol) (PEG), P(PF-co-EG), synthesizing a PEG-tethered fumarate (PEGF), coupling agmatine sulfate to the PEGF to produce PEGF modified with agmatine (Agm-PEGF), and synthesizing a hydrogel by cross-linking P(PF-co-EG) with Agm-PEGF. Preferred techniques for carrying out each of the foregoing steps are set out in detail below.

In quantitative tests on hydrogels produced according to the present techniques, it was found that the weight swelling ratio of these hydrogels at pH 7.0 increased from 279±4 to 306±7% as the initial Agm-PEGF content increased from 0 to 200 mg/g of P(PF-co-EG), respectively. The diffusional exponents, n, during the initial phase of water uptake were independent of the initial Agm-PEGF content and were determined to be 0.66±0.08, 0.71±0.07, and 0.60±0.05 for respective initial Agm-PEGF contents of 0, 100, and 200 mg/g. The heat of fusion of water present in the hydrogels increased from 214±11 to 254±4 J/g as the initial Agm-PEGF content increased from 0 to 200 mg/g. The number of adherent smooth muscle cells increased dose-dependently from 15±6 to 75±7% of the initial seeding density as the initial Agm-PEGF content increased from 0 to 200 mg/g. These results suggest that the incorporation of the guanidino groups of agmatine into P(PF-co-EG) hydrogels increases hydrogel free water content and the total water content of the hydrogels and also enhances cell adhesion to the hydrogels.

The incorporation of Agm-PEGF into P(PF-co-EG) hydrogels was shown qualitatively by staining the hydrogels with BPB. BPB has one sulfonyl group and is negatively charged at pH 6.8, the range at which the BPB staining was performed. Hydrogels without staining showed no absorbance at 590 nm. Experimental results suggest that the Agm-PEGF is incorporated into the hydrogel dose-dependently. Only a slight amount of the Agm-PEGF was detected. This result suggests that cross-linking is not sufficient for the incorporation of the feed Agm-PEGF into hydrogels, or that Agm-PEGF or the guanidino groups degrade during cross-linking. Since the NMR spectrum indicates that all ester bonds of Agm-PEGF were not hydrolyzed after the Agm-PEGF was dried from $ddH_2O$ by rotovaporation at 75° C., it may not be possible that Agm-PEGF degraded during cross-linking. Shin et al. demonstrated the enhanced adhesion of marrow stromal osteoblasts to hydrogels modified with Arg-Gly-Asp (RGD) peptides fabricated through radical cross-linking by redox initiators of ascorbic acid and ammonium persulfate. The amount of the incorporated RGD peptide was not quantified. However, the peptide maintained its function after the cross-linking reaction. These results suggest that the cross-linking does not affect the chemical structure of guanidino group. Therefore, the reason for the insufficient incorporation may be due to the low cross-linking reactivity of Agm-PEGF. Most ionic hydrogels reported previously are vinyl-based hydrogels. The double bond of fumarate is thought to be less reactive than that of vinyl group because of the electroinductive effect of the carbonyl groups. In addition, P(PF-co-EG) is a block copolymer, and the cross-linkable fumarate unit exists in the hydrophobic portion of the copolymer. The cross-linkable fumarate of Agm-PEGF exists between PEG chains. Therefore, it is possible that the Agm-PEGF macromer's fumarate double bond may be sterically hindered the PPF portion of P(PF-co-EG) block copolymer. Another reason for the low Agm-PEGF content may be related to the reproducibility of the BPB staining method. Acid Orange 7 was used for quantification of positive charge contents in cationically modified surface and poly(acrylamide-dimethylaminoethyl methacrylate) hydrogels by analyzing the extracted dye. Staining conditions, such as pH and time, may affect the results. Absorbance of the adsorbed BPB was measured directly, but the adsorption of BPB to the hydrogels may affect the spectroscopic characteristics of BPB. Further optimization is required for a quantitative analysis by this method.

We observed an increase in a swelling ratio with the initial Agm-PEGF content. Many studies of pH sensitive ionic hydrogels reported that incorporation of carboxyl groups or amine groups into hydrogels enhances the swelling ratio, depending on the content of the ionic groups and the pH and ionic strength of the buffers in which the hydrogels were swollen. In these previous reports, hydrogels were prepared at a molar ratio of ionic monomer to nonionic counterpart of at least 1 to 37.5, and the pKa of carboxyl and tertiary amino group were 5.5-5.9 and 7.7, respectively. The guanidino group content of agmatine-modified P(PF-co-EG) hydrogels was low as described above. For hydrogels fabricated with an initial Agm-PEGF content of 200 mg/g, the final molar ratio of the Agm-PEGF to P(PF-co-EG) copolymer was 1 to 260. Our results suggest that this molar ratio is sufficient to increase the hydrogel swelling.

The pH does not affect the swelling ratio of the hydrogels significantly within pH range of 5~9 because the pKa value of the guanidino group is 12.5. However, the swelling characteristics of degraded hydrogels may vary with the pH because of the dependence of the degradation rate on the pH. Iio et al. demonstrated that hydrogels made of poly(allylbiguanid-co-allylamine) and poly(vinyl alcohol) exhibited a shrinkage above pH 10 at the ionic strength of 0.1M, which resulted from the deprotonation of the biguanido groups. The initial content of the allyl biguanido groups was reported to be 18% in hydrogel preparation. It is expected that the swelling ratio of agmatine-modified P(PF-co-EG) hydrogels will decrease of pH values in the vicinity of the pKa value of the guanidino group.

Similarly, incorporation of up to 200 mg/g of initial Agm-PEGF did not significantly affect water diffusion into the hydrogel. Bajpai reported that the incorporation of small amount of maleic acid into poly(acrylamide) hydrogel resulted in the transition of the swelling mechanism from Fickian to non-Fickian diffusion, and that this transition was enhanced dose-dependently by the feed molar content of maleic acid. The diffusional exponent for P(PF-co-EG) hydrogels was about 0.66 and independent of the initial Agm-PEGF content, indicating that the water diffusion into the hydrogels appeared to follow non-Fickian diffusion. It is reported that ion-osmotic swelling pressure and chain relaxation caused by electrostatic repulsion between adjacent ionized groups are responsible for non-Fickian diffusion. Since even the unmodified hydrogel did not appear to follow Fickian diffusion, factors other than positive charges, such as a strong interaction of water with the copolymer PEG chain, may affect water transport.

In the DSC study described below, the guanidino groups affected the heat of fusion of the water existing in the hydrogels. Since the heat of fusion of pH 7.0 buffer alone was 335 J/g, it is suggested that a portion of the diffusing water is not at a free state but instead bound to the PEG chain of the copolymer. The guanidino groups inhibit water from binding to the PEG chain in a dose-dependent manner. We also observed a decrease in the enthalpy of crystallization of the PEG with an increase in the initial Agm-PEGF content of the hydrogels. This result suggests that the guanidino groups inhibit the interaction of PEG chains.

The incorporation of guanidino groups into P(PF-co-EG) hydrogel significantly enhanced smooth muscle cell adhesion in a dose dependent manner. This result suggests that the Agm-PEGF content is sufficient for cell adhesion. Smooth muscle cells were examined in this study because of the potential application of the modified hydrogel as an embolic biomaterial. Fibronectin and vitronectin have been reported to enhance cell adhesion and spreading. Their isoelectric points are 5.6-6.1 and 4.8-5.0, respectively, and they are negatively charged at physiological conditions. These proteins are thought to be adsorbed on the surface of the agmatine-modified hydrogels, and may play an important role in cell adhesion to the surface.

Agmatine is naturally synthesized from arginine by arginine decarboxylase and is metabolized via hydrolysis by agmatinase to putrecine and urea. Agmatine has been detected in various human tissues such as the brain, lung, stomach, and spleen, and is present at concentrations less than 100 ng/ml in human serum. Agmatine also exhibits diverse biological effects through imidazolin binding sites and α2-adrenergic receptors at much higher concentrations. The function of agmatine at a physiological concentration is not fully understood. However, it has been reported that agmatine exerted no cytotoxic effects at a concentration of 1 mM, while the lethal dose in a rat experimental model was 1-10 mg/kg. (6) Agmatine has two functional groups: a guanidino group and a primary amino group. The pKa value of the guanidino group is 12.5, allowing for protonation, and thus possession of a positive charge over a wide pH range. Moreover, the primary amino group has nucleophilicity and is useful for coupling reactions.

Experimental Section

Materials. Diethyl fumarate, propylene glycol, poly(ethylene glycol) (PEG), succinic anhydride, anhydrous pyridine, anhydrous methylene chloride, N-hydroxysuccinimide, and dicyclohexylcarbodiimide were purchased from Aldrich (Milwaukee, Wis.). Hydroquinone was purchased from Acros (Pittsburgh, Pa.). Zinc chloride, methylene chloride, 2-propanol, n-hexane, toluene, and diethyl ether were purchased from Fisher Scientific (Pittsburgh, Pa.). Agmatine sulfate, bromophenol blue, and ascorbic acid were purchased from Sigma (St. Louis, Mo.). A human aortic smooth muscle cell line (CRL-1999) was purchased from American Type Culture Collection (Manassas, Va.). Dulbecco's modified Eagle medium (DMEM), and phosphate buffered saline (PBS) were purchased from Gibco/Life technologies (Gaithersburg, Md.). Fetal bovine serum (FBS) was purchased from Gemini Bioproducts (Calabasas, Calif.).

Methods. Copolymer synthesis. Poly(propylene fumarate) (PPF) was synthesized as described in Shung, A. K.; Timmer, M. D.; Jo, S.; Engel, P. S.; Mikos, A. G. *J. Biomater. Sci. Polym. Edn.*, which is incorporated herein in its entirety (18). Briefly, diethylfumarate was vigorously mixed with a 3-fold molar excess of propylene glycol at 160° C. in the presence of hydroquinone and zinc chloride. The reaction was performed under a nitrogen blanket. Transesterification of the intermediate fumaric diester was performed at 150° C. under a vacuum of 0.1 mmHg under vigorous stirring. Poly(ethylene glycol) of nominal molecular weight 600 was added to the reaction vessel under the same conditions to form the copolymer. The resulting copolymer was precipitated from methylene chloride with 2-propanol. The copolymer was recovered with a separation funnel and dried under reduced pressure. The molecular weight of the purified copolymer was determined by gel permeation chromatography (GPC) using polystyrene standards for a universal calibration curve as previously described. (9)

Poly(ethylene glycol)-tethered fumarate synthesis. One hundred grams of diethylfumarate (0.6 mol) were vigorously mixed with 350 g of poly(ethylene glycol) of nominal molecular weight 300 (PEG300) (1.2 mol) at 160° C. in the presence of 0.4 g of hydroquinone and 1.5 g of zinc chloride. The reaction was performed under nitrogen gas flow for 5 hours. The resulting mixture was washed with a 5-fold volume of 2-propanol/n-hexane (2:3). PEG-tethered fumarate (PEGF) was separated from the solvents with a separation funnel and dried under reduced pressure. The molecular weight of the PEGF was determined by GPC.

Coupling of agmatine sulfate to poly(ethylene glycol)-tethered fumarate. One hundred grams of the PEGF (0.1 mol) were dried by azeotropic distillation with 800 ml of toluene. Thirty three grams of succinic anhydride (0.3 mol) and 27 ml of anhydrous pyridine (0.3 mol) were dissolved into 700 ml of anhydrous methylene chloride, and then added to the dried PEGF. The reaction mixture was refluxed at 60° C. for 24 hours. The solvent was removed by rotovaporation and the residue was washed twice with diethyl ether. After dissolution into 220 ml of anhydrous methylene chloride/diethyl ether (3:5), the residue was kept at −15° C. for 1 hour to precipitate the unreacted succinic anhydride. After the removal of unreacted succinic anhydride by filtration, the succinylated PEGF was obtained by evaporating the solvent.

Thirty grams of the succinylated PEGF (0.03 mol) and 9.6 g of N-hydroxysuccinimide (NHS) (0.08 mol) were dissolved into 500 ml of anhydrous methylene chloride. Seventeen grams of dicyclohexylcarbodiimide (DCC) (0.08 mol) were dissolved into 100 ml of anhydrous methylene chloride. The reaction was performed for 24 hours at room temperature under vigorous mixing. After the removal of precipitated dicyclohexyl urea by filtration, the crude product was obtained by rotovaporation. The succinylated PEGF activated with NHS (NHS-PEGF) was obtained after washing with ether. The product was further dried to remove any remaining ether.

Five grams of NHS-PEGF (5 mmol) were dissolved in 25 ml of N,N-dimethylformamide (DMF). After 2.2 g of agmatine sulfate (10 mmol) were dissolved in 50 ml of 0.1 N sodium bicarbonate buffer (pH 8.3), the former solution was added drop-wise to the latter solution in an ice bath and stirred at room temperature for another 29 hours. The reaction mixture was diluted with 75 ml of deionized distilled water (ddH$_2$O) and the solution was transferred into a cellulose ester dialysis membrane (SpectroPro® MWCO 500, Spectrum Laboratories, Rancho Dominguez, Calif.) and dialyzed by using ddH$_2$O for 3 days at room temperature with periodic water changes. After dialysis, ddH$_2$O was removed by rotovaporation at 75° C. PEGF modified with agmatine (Agm-PEGF) was obtained after drying under a reduced pressure. PEGF, succinylated PEGF, NHS-PEGF, and Agm-PEGF were characterized by a $^1$H-NMR spectrometer (Bruker AC 400 MHz Wide Bore NMR spectrometer).

Hydrogel synthesis. Cross-linking was performed by a radical reaction using a redox initiator. In a typical experiment, 1 g of P(PF-co-EG) of number average molecular weight of 5300, various Agm-PEGF contents and 100 μL of 1 M ammonium persulfate were dissolved in 2 mL of ddH$_2$O. PEGF was added to the solution to adjust the total macromer content of Agm-PEGF and PEGF to 200 mg. Then 100 μL of 1 M ascorbic acid was added to the solution. A film was fabricated by pouring the resulting solution between two glass plates separated by a 1 mm gap. Cross-linking was performed overnight at 37° C. The films were immersed in ddH$_2$O overnight with periodic medium changes to remove the unreacted polymer and macromer. The swollen films were cut into disks of different diameters as described below for further analysis.

Characterization of Hydrogels

Agmatine content measurement by bromophenol blue staining. A bromophenol blue (BPB) solution was made by dissolving 5 mg of BPB into 45 ml of 10 mM Tris-HCl buffer (pH 6.8). Hydrogels of 4 mm in diameter were swollen in ddH$_2$O. The hydrogels were stained in 2 ml of the BPB solution for 25 hours at 37° C. Excess BPB was removed by a rinse with 10 mM Tris-HCl buffer (pH 6.8) at room temperature. The stained hydrogel was placed into a 96 well polystyrene microplate. The absorbance of BPB was measured at 590 and 700 nm by PowerWaveX340 microplate scanning spectrophotometer (BIO-TEK®Instruments Winooski, Vt.) with KCjunior™ analytical software. Since BPB has a strong absorbance at 590 nm and no absorbance at 700 nm, a background was corrected by subtracting the absorbance at 700 nm from the absorbance at 590 nm. Hydrogels treated with 10 mM Tris-HCl (pH 6.8) without BPB were used as controls. For a quantitative analysis, a calibration curve was obtained by measuring the absorbance of standard BPB solutions, prepared by dissolving various amounts of BPB into 10 mM Tris-HCl buffer (pH 6.8). Twenty eight microliters of these BPB solution were placed onto a 96-well microplate to give a volume with the same thickness as swollen hydrogels, approximately 1 mm, in a well. Agm-PEGF content in the hydrogels was calculated from the absorbance data, the dry weights of hydrogels, and the molecular weights of BPB and Agm-PEGF (691.95 and 1068, respectively).

Swelling ratio measurement. Water swollen hydrogels (4 mm in diameter) were air-dried for 48 hours, and then the hydrogel dry weight was measured. The weight of the swollen hydrogels was measured after swelling the dry films in buffers of various pH of which ionic strength was 0.1M at 25° C. for more than 24 hours. The following buffers were used for this experiment: sodium acetate buffer of pH 5.0, sodium phosphate buffers of pH 6.0 and pH 7.0, Tris-HCl buffers of pH 8.0 and pH 9.0. Sodium chloride was used to adjust the ionic strength to 0.1M. The swelling ratio was calculated using the following equation:

Swelling ratio (%)=(wet weight)/(dry weight)×100

Hydrogel degradation. Degradation of hydrogels was determined by the gravimetric method. Swollen 8.5 mm diameter hydrogels as described above. The hydrogels were then placed in 2 ml of buffer of pH of 5.0, 7.0 or 9.0 at 37° C. on a rotating shaker. The buffers were changed for all samples every 12 hours until the third day and every day thereafter to keep the pH relatively constant. The hydrogels were removed at 3 and 7 days, rinsed with deionized distilled water, and air-dried for 48 hours. The dry weight was measured and normalized with the initial dry weight.

Differential scanning calorimetry. Differential scanning calorimetry (DSC) analysis was performed with a TA Instruments Model 2920 modulated differential scanning calorimetry with a mechanical cooling accessory (Newcastle, Del.), as is known in the art. A dry hydrogel film (4 mm in diameter) was swollen in sodium phosphate buffer of pH 7.0. The swollen film (8 to 10 mg) was placed in an aluminum pan, sealed hermetically, and then cooled in liquid nitrogen for 1 minute. The pan was heated at 5° C./min from −60° C. to 50° C. The enthalpy of PEG crystallization was determined from the exothermic peak area. Since endotherms from −20° C. to 15° C. result from the melting of water PEG crystals, the heat of fusion ($\Delta H_f$) of water was determined by subtracting the enthalpy of PEG crystallization from the integrated endothermic peak area.

Water diffusion into hydrogels. Water swollen hydrogels (5.5 mm diameter) were dried as described above. A dried hydrogel was placed into sodium phosphate buffer of pH 7.0 and ionic strength of 0.1M at 25° C. The water uptake was followed by measuring the weight gain as a function of time at 0.5, 1, 2, 3, 4, 5 10, 20, 30, 60, 180 min after immersion. Water uptake at equilibrium was measured more than 24 hours after immersion. The following equation was used to characterize the diffusion process of P(PF-co-EG) hydrogel films.

$$M_t/M_\infty = kt^n \text{ for } 0 < M_t/M_\infty < 0.6 \qquad (1)$$

In this equation, $M_t$ and $M_\infty$ correspond to the water uptake at time t and at equilibrium, respectively. The constant k is related to the structure of hydrogels and n is a diffusional exponent determined from the slope of the linear regression of $\ln(M_t/M_\infty)$ vs. $\ln(t)$.

Smooth muscle cell attachment. Smooth muscle cells were cultured in DMEM in the presence of 10% FBS at 37° C. in a humidified 5% CO$_2$ atmosphere. Ascorbic acid was added to the medium at a concentration of 50 μg/mL. Cells of passage 3 were used in the adhesion study.

Hydrogel disks of 20 mm in diameter were sterilized with dehydrated ethanol in a 12 well microplate for more than 12 hours. Each disk was immersed in 2 ml of PBS in a 12 well tissue culture dish overnight to remove the ethanol. After rinsing the disk twice with 2 ml of PBS, a stainless steel ring (2.2 mm outside diameter, 1.6 mm inside diameter, 1.6 mm height) was placed on the top of the disk to prevent the disk from floating. Smooth muscle cells were suspended in DMEM in the presence of 10% FBS. One mililiter of the cell suspension was placed onto each disk and kept at 37° C. for 20 h under static conditions. The initial seeding density was $7.0 \times 10^3$ cells/cm$^2$. After 20 h, the medium was removed, and the disk was rinsed twice with 2 mL of serum-free DMEM. Adhered cells were lifted from the disk with 0.05% trypsin in DMEM, and the lifted cells were suspended in 0.1 mL of DMEM containing 10% FBS. The number of adhered cells was counted with a Multisizer™3 Coulter Counter (Beckman).

Statistics. Statistical analysis was performed with Student's unpaired t-test with a 95% confidence interval (P<0.05). Three repetitions were performed for all experiments. The data are reported as means±standard deviation (SD).

Results

Molecular weights of PEG 300, PEG-tethered fumarate (PEGF), succinylated PEGF, and the succinimidyl ester of succinylated PEGF produced using the techniques described above are given in Table 1. All data were obtained by GPC. Number average molecular weight ($M_n$) and weight average molecular weight ($M_w$) were based on polystyrene standards in chloroform.

TABLE 1

|  | $M_n$ | $M_w$ |
| --- | --- | --- |
| PEG 300 | 600 | 600 |
| PEG-Tethered Fumarate | 1300 | 1700 |
| Succinylated PEGF | 1500 | 2000 |
| Succinimidyl Ester of PEGF | 1900 | 2400 |

Quantitative analysis of the NMR spectrum showed that 98% of the two carboxyl groups of the fumarate were esterified with PEG300. GPC measurements showed that the number average molecular weights ($M_n$) of PEGF and PEG300 were 1300 and 600, respectively.

An $^1$H-NMR spectrum of PEGF after succinylation, and in particular proton peaks at 4.2 ppm and 2.6 ppm, indicated the methylene group of PEGF attached to succinic anhydride and the methylene group of succinate, respectively. The calculated conversion yield of the esterification was 90%. The number average molecular weight of succinylated PEGF was determined to be 1500 by GPC. The NMR spectrum indicates that the reaction product contains free succinic anhydride and residual pyridine, which were identified at 2.8 ppm and 7.3-8.6 ppm, respectively. The number average molecular weight of the succinimidyl ester of the succinylated PEGF determined by GPC was 1900.

NMR spectra of the succinylated PEGF, the Agm-PEGF, and agmatine in D$_2$O indicated methylene proton peaks of the succinate attached to agmatine at 2.5 ppm and 2.6 ppm, while the methylene proton peak of agmatine attached to the succinimidyl ester appears at 3.1-3.2 ppm. The coupling yield of agmatine to NHS-PEGF was determined to be about 100% by NMR. Peaks at 1.6-1.8 ppm and 2.9-3.0 ppm indicated unreacted agmatine.

Hydrogel Staining with BPB.

Figure 2:
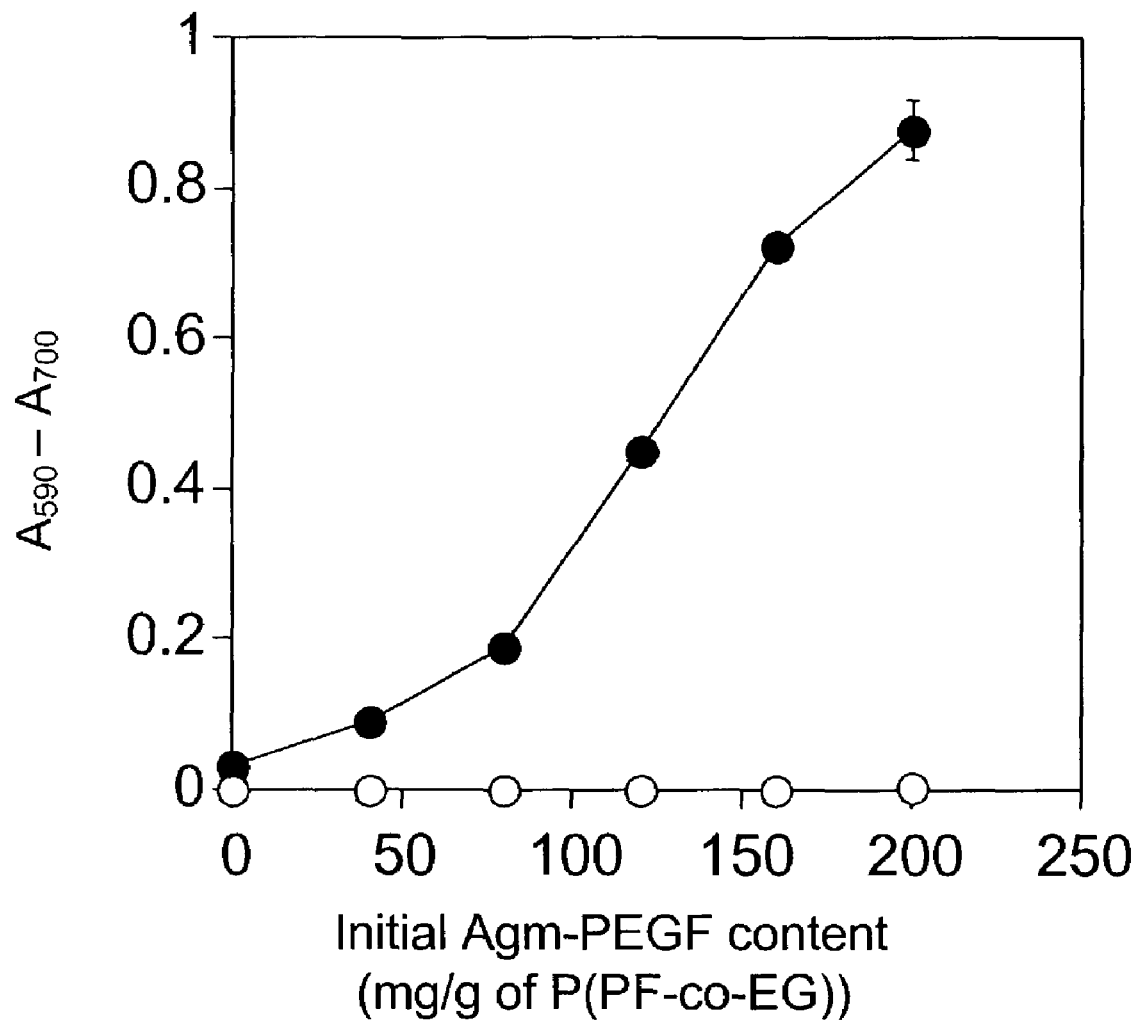
FIG. 2 is a plot showing the variation of BPB (bromophenol blue) adsorption onto P(PF-co-EG) hydrogels versus initial Agm-PEGF content.

Hydrogels with and without agmatine were stained by bromophenol blue (BPB). The variation of BPB adsorption onto P(PF-co-EG) hydrogels varied with the initial Agm-PEGF content as shown in FIG. 2. The hydrogels were treated with Tris-HCl buffer in the presence (●) and absence (○) of BPB for 25 hours at 37° C. The absorbance of the adsorbed BPB was measured at 590 nm ($A_{590}$) and corrected for background absorbance by subtracting the absorbance at 700 m ($A_{700}$). Error bars correspond to means±SD for n=3. The absorbance of the adsorbed BPB increased with the amount of Agm-PEGF. Hydrogels without staining did not have absorbance at 590 nm, even though they incorporated agmatine. The amount of agmatine incorporated in hydrogels was determined to be less than 0.4% by using a calibration curve for the range of initial Agm-PEGF contents examined, as set out in Table 2.

TABLE 2

Agm-PEGF content of P(PF-co-EG) hydrogel determined by BPB staining method.

| Intial Agm-PEGF content | (mg/g)[b] | 0 | 40 | 80 | 120 | 160 | 200 |
| --- | --- | --- | --- | --- | --- | --- | --- |
| Actual Agm-PEGF content[a] | (mg/g)[b] | 0.00 | 0.04 | 0.13 | 0.25 | 0.50 | 0.77 |

[a]determined by BPB staining method
[b]weight ratio of Agm-PEGF to P(PF-co-EG)

Swelling Behavior.

Figure 3:
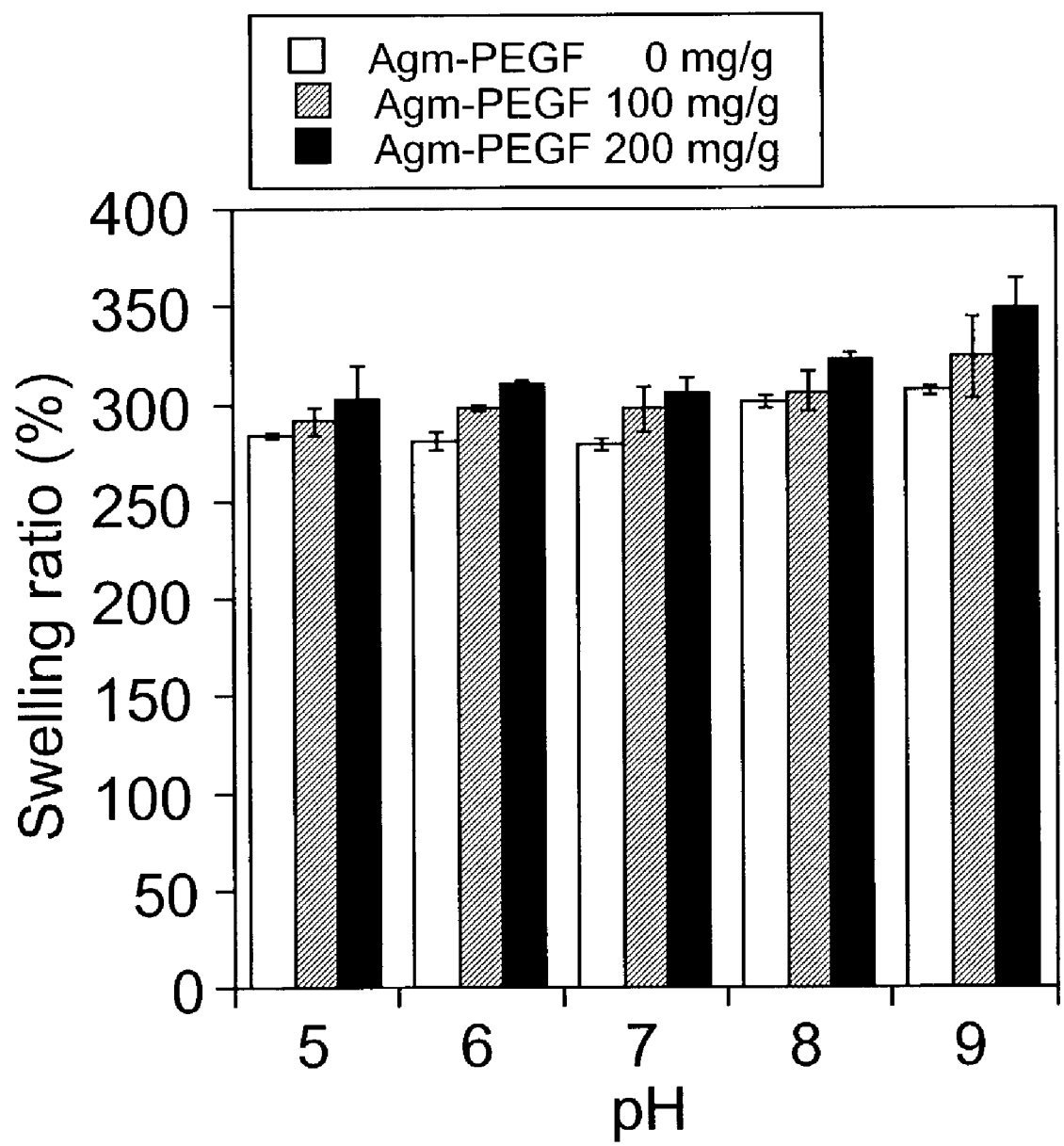
FIG. 3 is a plot showing the variation of the weight swelling ratio of P(PF-co-EG) hydrogels with the pH of the swelling buffer as a function of the initial Agm-PEGF content.

FIG. 3 illustrates the effect of pH on the weight swelling ratio of P(PF-co-EG) hydrogels as a function of the initial Agm-PEGF content. Error bars correspond to means±SD for n=3. The swelling ratio slightly increased with the initial Agm-PEGF content at every pH. However, the swelling ratio did not vary significantly with the pH.

Figure 4:
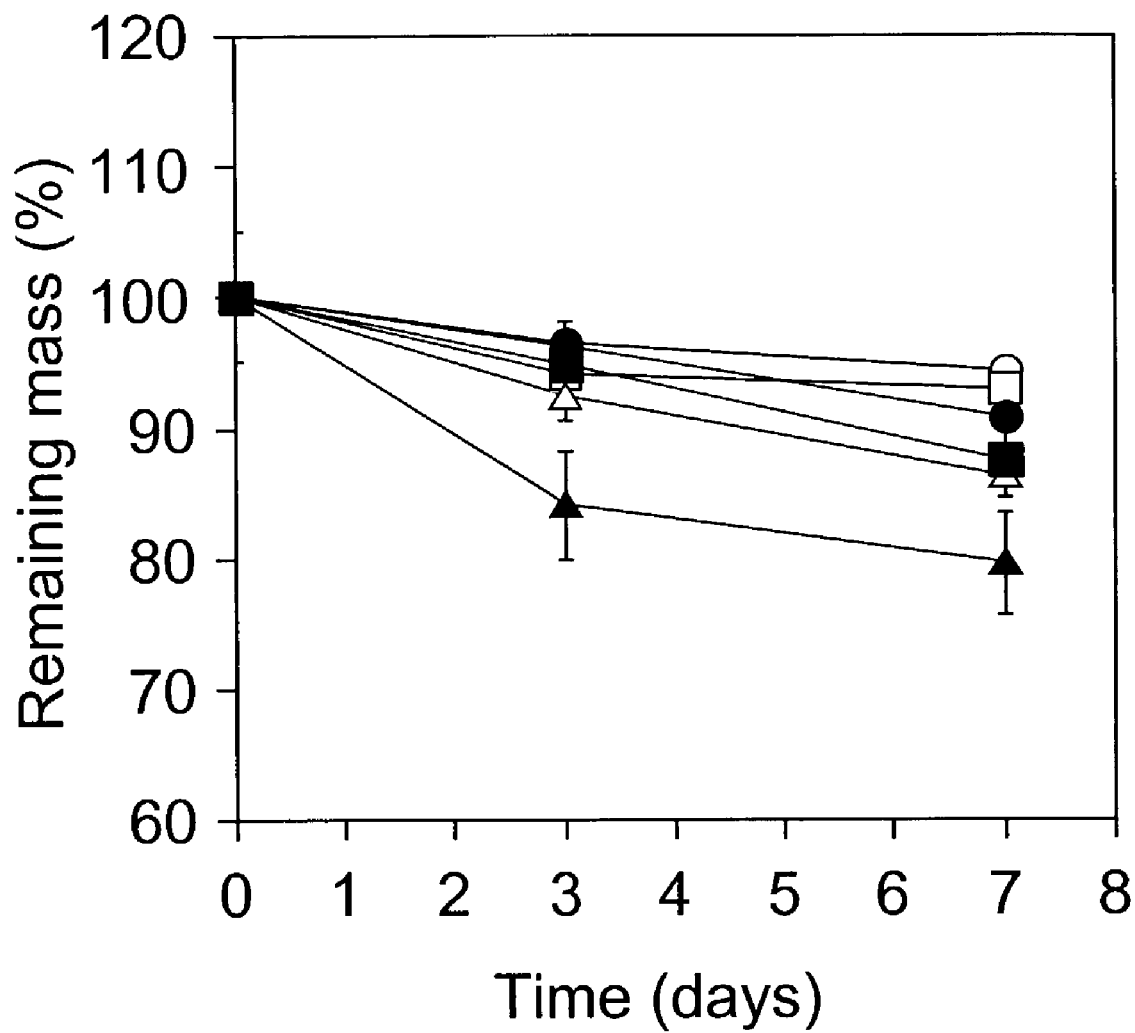
FIG. 4 is a plot showing the variation over time of the remaining mass of P(PF-co-EG) hydrogels at various pH.

FIG. 4 shows the effect of pH on the degradation of the hydrogels with the initial Agm-PEGF contents of 0 and 200 mg/g and specifically the variation of the remaining mass of P(PF-co-EG) hydrogels at various pH versus the incubation time. The hydrogels with initial Agm-PEGF contents of 0 mg/g (○,△,□) and 200 mg/g (●,▼,■) were placed in buffers at pH 5.0 (○,●), 7.0 (△,▼), and 9.0 (□,■). Error bars correspond to means±SD for n=3. The normalized remaining mass decreased with time, and a decrease in the remaining mass was larger at pH 9.0 than at pH 5.0 and 7.0.

Figure 5:
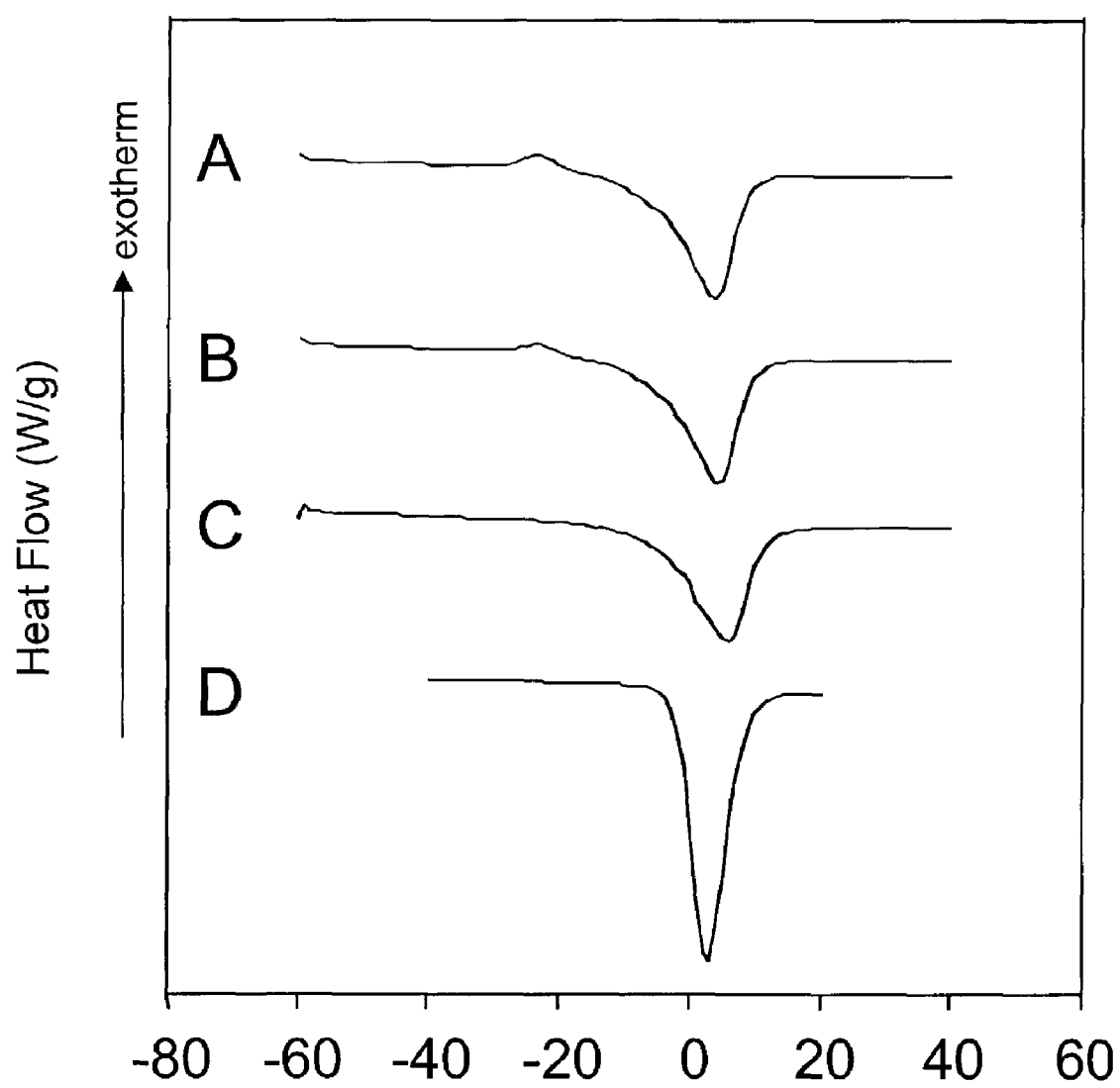
FIG. 5 is a plot of four DSC thermograms of P(PF-co-EG) hydrogels with initial Agm-PEGF contents of 0 mg/g (A), 100 mg/g (B), and 200 mg/g (C) swollen in sodium phosphate buffer of pH 7.0 and heated from −60 to 50° C. at 5° C./min, and an exotherm of the buffer alone (D)

FIG. 5 shows DSC thermograms of P(PF-co-EG) hydrogels with initial Agm-PEGF contents of 0 mg/g (A), 100 mg/g (B), and 200 mg/g (C) swollen in sodium phosphate buffer of pH 7.0 and heated from −60 to 50° C. at 5° C./min. The thermogram of the buffer alone is also shown (D). The exotherm corresponds to crystallization of PEG. The endotherm corresponds to melting of water and PEG crystals. The exothermic peak resulting from cold crystallization of PEG was observed on the thermogram of the hydrogel.

The enthalpy of crystallization decreased with the initial Agm-PEGF content, as shown by the results in Table 3. The heat of fusion of water was significantly higher for hydrogels with an initial Agm-PEGF content of 200 mg/g compared to hydrogels without Agm-PEGF. The heat of fusion of pH 7.0 buffer alone was 335 J/g.

TABLE 3

Variation of heat of fusion of water, enthalpy of crystallization, and diffusional exponent of water (from equation 1) of P(PF-co-EG) hydrogels with the initial Agm-PEGF content (means ± SD for n = 3).

| Initial Agm-PEGF content[a] (mg/g) | Heat of fusion of water (J/g) | Enthalpy of crystallization of PEG (J/g) | Diffusional exponent |
|---|---|---|---|
| 0 | 214 ± 11 | 56 ± 3 | 0.66 ± 0.08 |
| 100 | 240 ± 4 | 30 ± 10 | 0.71 ± 0.07 |
| 200 | 254 ± 4 | 4 ± 8 | 0.60 ± 0.05 |

[a] weight ratio of Agm-PEGF to P(PF-co-EG)

Figure 6:
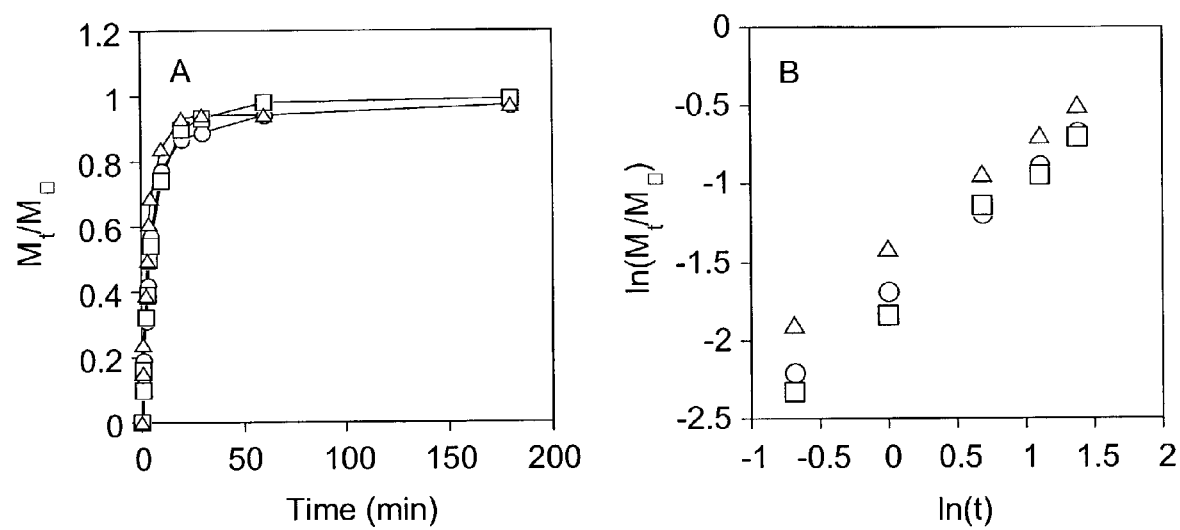
FIGS. 6A-B are plots illustrating the kinetics of the water sorption into P(PF-co-EG) hydrogels with initial Agm-PEGF contents of 0 mg/g (○), 100 mg/g (Δ) and 200 mg/g (□), where

FIG. 6 shows the kinetics of water sorption into P(PF-co-EG) hydrogels with initial Agm-PEGF contents of 0 mg/g (○), 100 mg/g (Δ) and 200 mg/g (□). Linear plot for the overall timecourse (FIG. 6A) and double logarithmic plot for the early phase (FIG. 6B) are shown. The timecourse gravimetry was performed in triplicate, and a typical example is shown for each case. The water diffusion was biphasic (FIG. 6A). In order to analyze the diffusion process in the early phase (0-4 min), where the ratio of $M_t/M_\infty$ was lower than 0.6, $\ln(M_t/M_\infty)$ was plotted against $\ln(t)$ (FIG. 6B). The slope of the linear regression gave the diffusional exponent, n. The diffusional exponents were not significantly different among hydrogels with various initial Agm-PEGF contents (Table 3, above). They were higher than 0.5, independent of the Agm-PEGF content.

Smooth Muscle Cell Adhesion.

Figure 7:
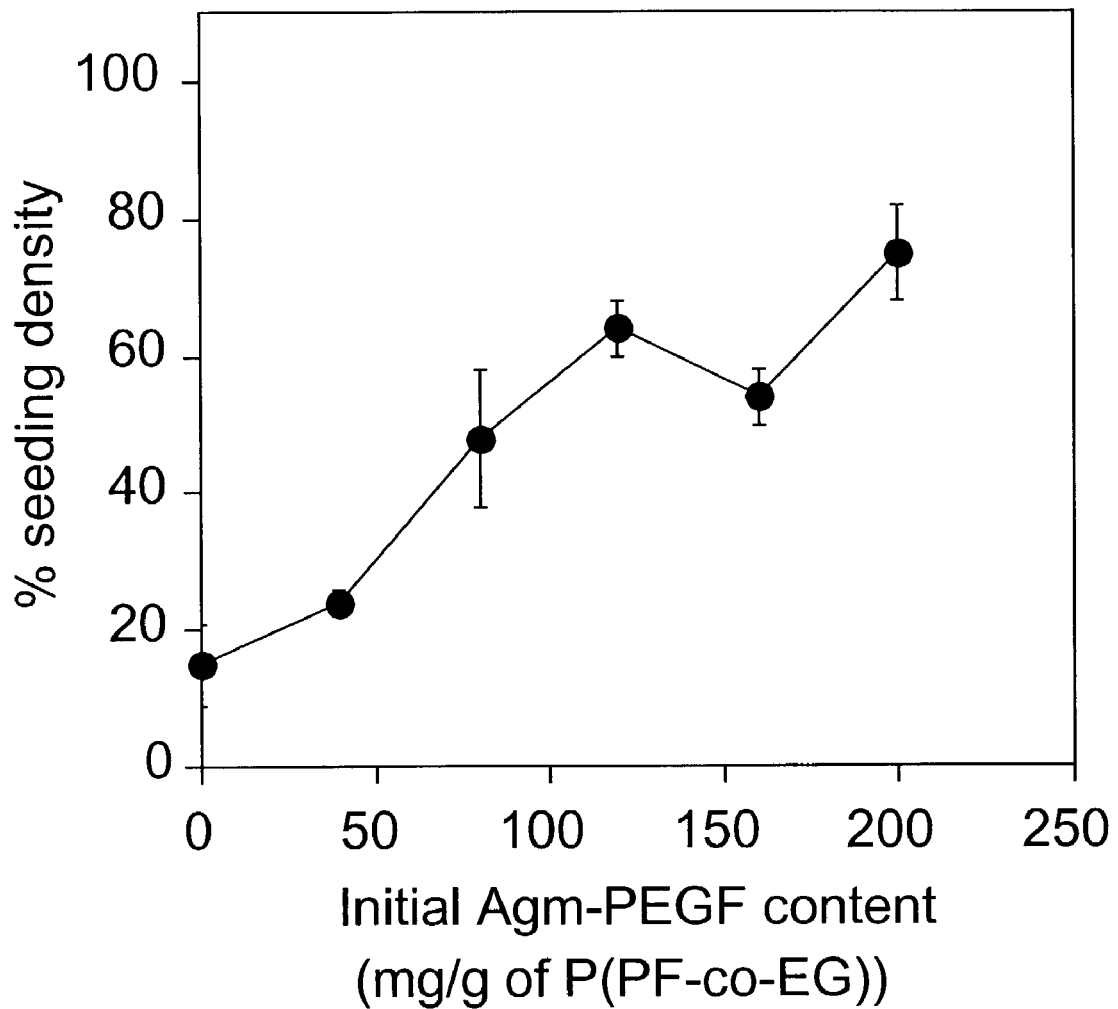
FIG. 7 illustrates the variation of vascular smooth muscle cell adhesion on P(PF-co-EG) hydrogels with the initial Agm-PEGF content.

FIG. 7 shows the variation of vascular smooth muscle cell adhesion on P(PF-co-EG) hydrogels with the initial Agm-PEGF content. The assay was performed in DMEM in the presence of 10% fetal bovine serum. The data were normalized with the initial seeding density. Error bars correspond to means±SD for n=3. The number of cells adhered to the hydrogels increased dose-dependently as the initial Agm-PEGF content increased up to 200 mg/g. The number of cells that adhered when the initial Agm-PEGF content was 200 mg/g was five times greater than the number that adhered in the absence of the Agm-PEGF.

As set out herein, a hydrogel having improved cell adhesion properties can be fabricated by crosslinking a copolymer of poly(propylene fumarate) and polyethylene glycol with agmatine. Hydrogels fabricated in this manner are particularly useful for regenerative medicine, drug delivery, and cell culture.

While preferred embodiments have been disclosed herein, it will be understood that the methods and compositions discussed herein can be varied without departing from the scope of the present invention. For example, hydrogels can be fabricated by crosslinking oligo(poly(ethylene glycol) fumarate) with agmatine. It will further be understood that the sequential recitation of steps in the claims is not intended to be a requirement that the steps be provided sequentially, or that any particular step be completed before commencement of another step.

All references cited herein are incorporated herein in their entireties, except that to the extent that definitions provided therein diverge from definitions provided in the present disclosure they are not adopted.

REFERENCES

1. Kikuchi, A.; Kataoka, K.; Tsuruta, T. *J. Biomater. Sci. Polym. Edn.* 1992, 3, 253-260.
2. Mori, Y.; Nagaoka, S.; Kikuchi, T.; Tanzawa, H. *J. Biomed. Mater. Res.* 1982, 16, 209-218.
3. Augusta, S.; Gruber, H. F.; Streichsbier, F. *J. Appl. Polym. Sci.* 1994, 53, 1149-1163.
4. Lemieux, P.; Vinogradov, S. V.; Gebhart, C. L.; Guerin, N.; Paradis, G.; Nguyen, H. K.; Ochietti, B.; Suzdaltseva, Y. G.; Bartakova, E. V.; Bronich, T. K.; St-Pierre, Y.; Alakhov, V. Y.; Kabanov, A. V. *J. Drug. Target.* 2000, 8, 91-105.
5. Godbey, W. T.; Wu, K. K.; Mikos, A. G. *J. Control. Release.* 1999, 60, 149-160.
6. Raasch, W.; Schafer, U.; Chun, J.; Dominiak, P. *Br. J. Pharmacol.* 2001, 133, 755-780.
7. Blantz, R. C.; Satriano, J.; Gabbai, F.; Kelly, C. *Acta. Physiol. Scand.* 2000, 168, 21-25.
8. Reis, D. J.; Regunathan, S. *Ann. N.Y. Acad. Sci.* 1999, 881, 65-80.
9. Suggs, L. J.; Payne, R. G.; Yaszemski, M. J.; Alemany, L. B.; Mikos, A. G. *Macromolecules.* 1997, 30, 4318-4323.
10. Suggs, L. J.; Kao, E. Y.; Palombo, L. L.; Krishnan, R. S.; Widmer, M. S.; Mikos, A. G. *J. Biomater. Sci. Polym. Edn.* 1998, 9, 653-666.
11. Suggs, L. J.; Krishnan, R. S.; Garcia, C. A.; Peter, S. J.; Anderson, J. M.; Mikos, A. G. *J. Biomed. Mater. Res.* 1998, 42, 312-320.
12. Suggs, L. J.; Mikos, A. G. *Cell Transplantation.* 1999, 8, 345-350.
13. Suggs, L. J.; Shive, M. S.; Garcia, C. A.; Anderson, J. M.; Mikos, A. G. *J. Biomed. Mater. Res.* 1999, 46, 22-32.
14. Suggs, L. J.; West, J. L.; Mikos, A. G. *Biomaterials.* 1999, 20, 683-690.
15. Tanahashi, K.; Mikos, A. G. *J. Biomed. Mater. Res.* 2002, 62, 558-566.
16. Shung, A. K.; Timmer, M. D.; Jo, S.; Engel, P. S.; Mikos, A. G. *J. Biomater. Sci. Polym. Edn.* 2002, 13, 95-108
17. Torres-Lugo, M.; Peppas, N. A. *Macromolecules.* 1999, 32, 6646-6651.
18. Jo, S.; Engel, P. S.; Mikos, A. G. *Polymer.* 2000, 41, 7595-7604.
19. Shin, H.; Jo, S.; Mikos, A. G. *J. Biomed. Mater. Res.* 2002, 61, 169-179.
20. Kulik, E.; Ikada, Y. *J. Biomed. Mater. Res.* 1996, 30, 295-304.
21. Ruiz, J.; Mantecón, A.; Cadiz, V. *Polymer.* 2001, 42, 6347-6354.
22. Bajpai, S. K. *J. App. Polym. Sci.* 2001, 80, 2782-2789.
23. Gemeinhart, R.; Chen, J.; Park, H.; Park, K. *J. Biomater. Sci. Polym. Edn.* 2000, 11, 1371-1380.
24. Baker, D. A.; Corkhill, P. H.; Ng, C. O.; Skelly, P. J.; Tighe, B. *J. Polymer.* 1988, 29, 691-700.
25. Khare, A. R.; Peppas, N. A. *Polymer.* 1993, 34, 4736-4739.
26. Baker, J. P.; Blanch, H. W.; Prausnitz, J. M. *J. App. Polym. Sci.* 1994, 52, 783-788.

27. Iio, K.; Minoura, N.; Nagura, M. *Polymer.* 1995, 36, 2579-2583.
28. Uchida, E.; Uyama, Y.; Ikada, Y. *Langmuir.* 1993, 9, 1121-1124.
29. Graham, N. B.; Zulfigar, M.; Nwachuku, N. E.; Rashid, A. *Polymer.* 1989, 30, 528-533.
30. Graham, N. B.; Zulfigar, M.; Nwachuku, N. E.; Rashid, A. *Polymer.* 1990, 31, 909-916.
31. Grinnell, F. *J. Cell. Biol.* 1980, 86, 104-112.
32. Grinnell, F. *J. Cell. Biol.* 1986, 103, 2697-2706.
33. Miyamoto, S.; Katz, B. Z.; Lafrenie, R. M.; Yamada, K. M. *Ann. N.Y. Acad. Sci.* 1998, 857, 119-129.
34. Felding-Habermann, B.; Cheresh, D. A. *Curr. Opin. Cell. Biol.* 1993, 5, 864-868.
35. Boughton, B. J.; Simpson, A. W. *Biochem. Biophys. Res. Commun.* 1984, 119, 1174-1180.
36. Vuento, M.; Korkolainen, M.; Kuusela, P.; Holtta, E. *Biochem. J.* 1985, 227, 421-427.
37. Whateley, J. G.; Knox, P. *Biochem. J.* 1980, 185, 349-354.

What is claimed is:

1. A cross-linkable monomer consisting of:
    a single fumaric acid moiety having a first end and a second end;
    a first spacer group affixed to said first end, wherein said first spacer group consists of one or more ethylene glycol units;
    a first terminal group affixed to said first spacer group;
    a second spacer group affixed to said second end, wherein said second spacer group consists of one or more ethylene glycol units; and
    a second terminal group affixed to said second spacer group,
    wherein said first and second terminal groups are selected from the group consisting of proteins, peptide sequences, and agmatine.

2. The cross-linkable monomer according to claim 1 wherein said first and second spacer groups are the same length.

3. The cross-linkable monomer according to claim 1 wherein said first spacer group and second spacer group are different lengths.

4. The cross-linkable monomer according to claim 1 wherein said first and second spacer groups each comprises at least three ethylene glycol units.

5. The cross-linkable monomer according to claim 1 wherein at least one of said first terminal group and said second terminal group is positively charged.

6. The cross-linkable monomer of claim 1 wherein said first terminal group comprises agmatine and said second terminal group is positively charged.

7. The cross-linkable monomer according to claim 1 wherein said first terminal group comprises agmatine and said second terminal group comprises peptide sequences, proteins, or combinations thereof.

8. The cross-linkable monomer according to claim 1 wherein said first terminal group and said second terminal group comprise agmatine.

9. A hydrogel formed by cross-linking a cross-linkable monomer, said cross-linkable monomer consisting of:
    a single fumaric acid moiety having a first end and a second end;
    a first spacer group affixed to said first end, wherein said first spacer group consists of one or more ethylene glycol units;
    a first terminal group affixed to said first spacer group;
    a second spacer group affixed to said second end, wherein said second spacer group consists of one or more ethylene glycol units; and
    a second terminal group affixed to said second spacer group,
    wherein said first and second terminal groups are selected from the group consisting of proteins, peptide sequences, and agmatine.

10. A hydrogel comprising an unsaturated monomer or macromer cross-linked a cross-linkable monomer, said cross-linkable monomer consisting of:
    a single fumaric acid moiety having a first end and a second end;
    a first spacer group affixed to said first end, wherein said first spacer group consists of one or more ethylene glycol units;
    a first terminal group affixed to said first spacer group;
    a second spacer group affixed to said second end, wherein said second spacer group consists of one or more ethylene glycol units; and
    a second terminal group affixed to said second spacer group,
    wherein said first and second terminal groups are selected from the group consisting of proteins, peptide sequences, and agmatine.

11. The hydro gel of claim 10 wherein said unsaturated macromer comprises poly(propylene fumarate-co-ethylene glycol) and said cross-linkable monomer comprises PEG-tethered fumarate (PEGF) modified with agmatine.

12. The hydro gel of claim 10 wherein said unsaturated macromer comprises poly(propylene fumarate-co-ethylene glycol), poly(propylene fumarate-co-propylene glycol), oligo(propylene fumarate-co-ethylene glycol), oligo(propylene fumarate-co-propylene glycol), oligo(poly(ethylene glycol) fumarate), oligo(poly(propylene glycol) fumarate), or combinations thereof.

13. A cross-linkable monomer consisting of:
    a single fumaric acid moiety having a first end and a second end;
    a first spacer group affixed to said first end, wherein said first spacer group consists of one or more ethylene glycol units;
    a first terminal group affixed to said first spacer group;
    a second spacer group affixed to said second end, wherein said second spacer group consists of one or more ethylene glycol units; and
    a second terminal group affixed to said second spacer group, wherein said first and second terminal groups each comprise a guanidino group.

14. The cross-linkable monomer of claim 13 wherein said first and second terminal groups each comprise agmatine.

15. The cross-linkable monomer of claim 13 wherein said first terminal group and said second terminal group each comprises an amino group.

16. A cross-linkable monomer consisting of:
    a single fumaric acid moiety having a first end and a second end;
    a first spacer group affixed to said first end, wherein said first spacer group consists of one or more ethylene glycol units;
    a first terminal group affixed to said first spacer group;
    a second spacer group affixed to said second end, wherein said second spacer group consists of one or more ethylene glycol units; and
    a second terminal group affixed to said second spacer group, wherein said first terminal group comprises agmatine and said second terminal group comprises acrylate or methacrylate.

17. A hydrogel formed by crosslinking a cross-linkable monomer, said cross-linkable monomer consisting of:
a single fumaric acid moiety having a first end and a second end;
a first spacer group affixed to said first end, wherein said first spacer group consists of one or more ethylene glycol units;
a first terminal group affixed to said first spacer group;
a second spacer group affixed to said second end, wherein said second spacer group consists of one or more ethylene glycol units; and
a second terminal group affixed to said second spacer group,
wherein said first terminal group is agmatine and said second terminal group is acrylate or methacrylate.

* * * * *

UNITED STATES PATENT AND TRADEMARK OFFICE
CERTIFICATE OF CORRECTION

PATENT NO. : 7,629,388 B2 Page 1 of 1
APPLICATION NO. : 10/300202
DATED : December 8, 2009
INVENTOR(S) : Antonios G. Mikos et al.

It is certified that error appears in the above-identified patent and that said Letters Patent is hereby corrected as shown below:

Claim 10, Col. 16, Line 10 replace "cross-linked a cross-linkable" with -- cross-linked with a cross-linkable --.

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,629,388 B2  Page 1 of 1
APPLICATION NO. : 10/300202
DATED : December 8, 2009
INVENTOR(S) : Mikos et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 788 days.

Signed and Sealed this

Second Day of November, 2010

David J. Kappos
*Director of the United States Patent and Trademark Office*